United States Patent
Chu et al.

(10) Patent No.: US 10,603,144 B2
(45) Date of Patent: *Mar. 31, 2020

(54) TRANSLUCENT VENEERING FOR A DENTAL PROSTHESIS FORMED BY A PRESS TO METAL PROCESS

(71) Applicant: DENTSPLY SIRONA Inc., York, PA (US)

(72) Inventors: Christopher C.Y. Chu, West Windsor, NJ (US); Slawomir Banasiak, Kearny, NJ (US)

(73) Assignee: Dentsply Sirona Inc., York, PA (US)

(*) Notice: Subject to any disclaimer, the term of this patent is extended or adjusted under 35 U.S.C. 154(b) by 792 days.

This patent is subject to a terminal disclaimer.

(21) Appl. No.: 14/338,442

(22) Filed: Jul. 23, 2014

(65) Prior Publication Data
US 2014/0327166 A1 Nov. 6, 2014

Related U.S. Application Data

(63) Continuation of application No. 13/934,584, filed on Jul. 3, 2013, now Pat. No. 8,821,162, which is a continuation of application No. 12/459,783, filed on Jul. 8, 2009, now Pat. No. 8,517,735, which is a continuation of application No. 11/788,600, filed as
(Continued)

(51) Int. Cl.
| | |
|---|---|
| *A61C 13/083* | (2006.01) |
| *A61C 13/08* | (2006.01) |
| *A61C 13/09* | (2006.01) |
| *A61K 6/02* | (2006.01) |

(52) U.S. Cl.
CPC ........ *A61C 13/0835* (2013.01); *A61C 13/081* (2013.01); *A61C 13/082* (2013.01); *A61C 13/09* (2013.01); *A61K 6/024* (2013.01); *A61K 6/025* (2013.01)

(58) Field of Classification Search
None
See application file for complete search history.

(56) References Cited

U.S. PATENT DOCUMENTS

| | | | | |
|---|---|---|---|---|
| 4,828,117 A | * | 5/1989 | Panzera | A61C 5/00 206/63.5 |
| 5,173,114 A | * | 12/1992 | Heurtaux | A61K 6/06 106/35 |

(Continued)

FOREIGN PATENT DOCUMENTS

WO    WO-02-00135 A1 *  1/2002

*Primary Examiner* — Matthew J Daniels
*Assistant Examiner* — Mohammad M Ameen
(74) *Attorney, Agent, or Firm* — Dentsply Sirona Inc.

(57) ABSTRACT

A dental prosthesis, typically formed in a press to metal process, includes application of a porcelain composition sufficient to form a veneer on a dental prosthesis supporting metal structure, the composition having an integrated tooth-like translucency providing an aesthetic appearance. The composition is formed of a dentin frit and an enamel frit, typically sintered into a desired ingot shape including an amount of composition sufficient to veneer the prosthesis. The porcelain composition is a component of a kit that includes opaquers, other porcelains and stains useful in finishing to provide an aesthetic prosthesis.

13 Claims, 1 Drawing Sheet

Related U.S. Application Data application No. PCT/US2006/055800 on Nov. 18, 2005, now abandoned.

(60) Provisional application No. 60/629,375, filed on Nov. 19, 2004.

(56) References Cited

U.S. PATENT DOCUMENTS

| | | | | |
|---|---|---|---|---|
| 5,713,994 A | * | 2/1998 | Kramer | A61K 6/0005 106/35 |
| 6,244,870 B1 | * | 6/2001 | Sakata | A61C 8/0048 106/38.22 |
| 8,517,735 B2 | * | 8/2013 | Chu | A61C 13/082 433/208 |

* cited by examiner

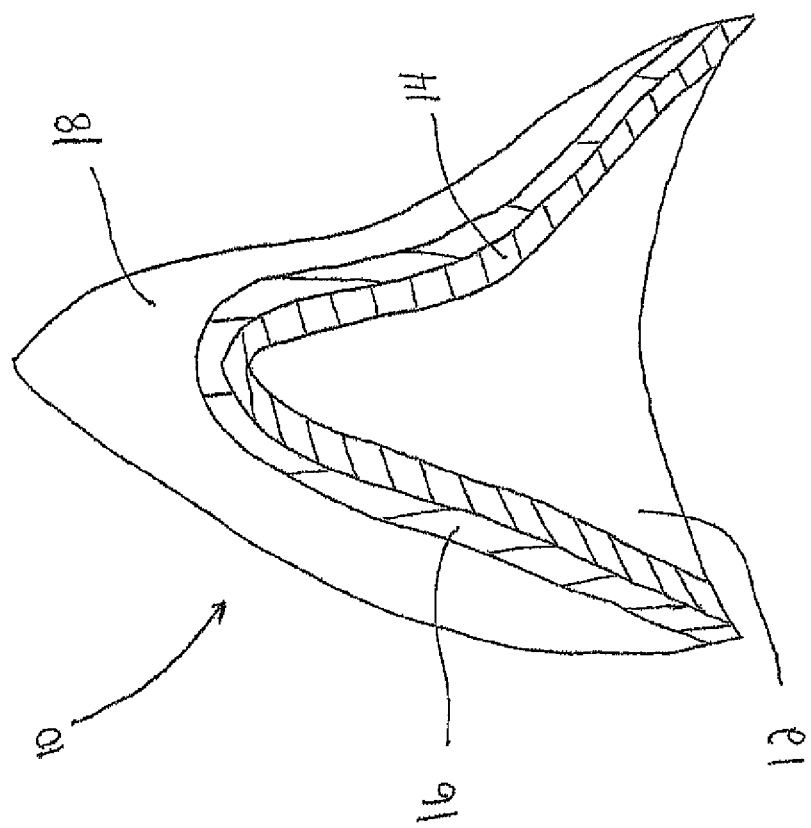

TRANSLUCENT VENEERING FOR A DENTAL PROSTHESIS FORMED BY A PRESS TO METAL PROCESS

RELATED APPLICATIONS

This application is a continuation of U.S. patent application Ser. No. 13/934,584, filed on Jul. 3, 2009, which is a continuation of U.S. patent application Ser. No. 12/459,783, filed on Jul. 8, 2009, now U.S. Pat. No. 8,517,735, which is a continuation of U.S. patent application Ser. No. 11/788,600, filed on Apr. 20, 2007, now abandoned, which is a continuation of International patent application Ser. No. PCT/US2006/055800, filed on Nov. 18, 2005, which claims the benefit of and priority to U.S. provisional application Ser. No. 60/629,375, filed on Nov. 19, 2004, which are herein incorporated by reference for all purposes.

FIELD OF THE INVENTION

The invention relates to dental prostheses comprising porcelain fused to a metal supporting structure or coping. Particularly, the invention relates to prostheses made by pressing a heated ceramic material into a mold onto said coping, wherein the mold is typically made by the lost wax process.

BACKGROUND OF THE INVENTION

A majority of crown and bridge restorations of teeth continue to be porcelain fused to a metal supporting structure or coping that provides strength for the prosthesis. While "all-ceramic" prostheses are of increasing importance, porcelain fused to metal (PFM) remains cost effective and provides satisfactory aesthetics.

Since the metal substructures used in these restorations are not naturally tooth colored, esthetic veneering porcelains are applied that mimic the color and form of natural teeth. The veneering process plays a critical role in providing a satisfactory restoration. Typically the process of making a PFM restoration requires an opaque layer for masking the metal coping; a dentin layer that simulates the color of the tooth dentin; and an enamel layer that simulates the transparency and neutral colors of the tooth enamel. Other materials such as stains are typically used to achieve aesthetic effects.

Each layer is typically applied by hand, first requiring mixing of selected porcelain powders and liquids. The result is subject to variability and depends upon careful work of a skilled ceramist. Achieving consistent, aesthetic results is time consuming and adds significant cost to the final product, as well as requiring people who have a scarce skill and necessary experience.

In a continuing drive to simplify processes and reduce labor costs, methods have been developed to replace the multi-stage porcelain veneering process by a process in which the veneer material is pressed onto the metal support. However, a remaining difficulty has been that the initial pressing must still often be followed by a hand layering with enamel porcelain, particularly to develop incisal edge translucency.

SUMMARY OF THE INVENTION

It is an object of the present invention to provide porcelain materials and processing methods wherein skilled, intensive, and costly hand layering is further reduced.

The invention is a dental prosthesis that includes a metal coping for supporting said prosthesis on tooth surfaces to be repaired. The metal coping is provided with an opaque layer that covers surfaces of the coping that would interfere with achieving an acceptable tooth-like appearance of the finished PFM. The opaque layer may be formed from a mixture of frits in powder or paste form and applied by spraying, a slurry dip, electrodeposit, or other forms or methods known to those skilled in the art. A porcelain layer, having an optimized, integrated translucency that blends dentin and enamel shades is fused to said opaqued surface by pressing the porcelain material onto said coping contained in a mold at fusing temperatures. The result is a strong and tough dental crown or bridge substructure that is veneered with porcelain having an integrated transparency, blending dentin and enamel character, such that further hand layering processes are eliminated or greatly reduced.

BRIEF DESCRIPTION OF THE DRAWINGS

FIG. 1. is a cross-sectional view of a dental prosthesis embodying concepts of the present invention.

DESCRIPTION OF THE PREFERRED EMBODIMENTS

The invention comprises a dental prosthesis, formed of elements, which may be supplied as components of a kit, that provide a porcelain fused to metal (PFM) restoration, using a pressing process to apply a finished surface instead of conventional hand layering of veneering porcelain. The veneering materials of the invention are designed for forming fixed prosthodontics devices that include both anterior and posterior crowns and bridges. Components of the kit, include principally: (1) dentin/enamel ingots having an integrated tooth-like translucency; and (2) opaquing porcelains, in both powder and paste forms, for covering metal coping surfaces that would otherwise be visible through the porcelain veneer. In addition, the kit may include enamel effect porcelains and glaze/stain porcelains for finishing the prosthesis, as necessary.

The veneering kit of the invention is intended for application to a wide range of supporting structure or coping alloys. For example, two commercially available alloys are non-precious NCM Alpha and Advantage, both manufactured by Austenal, formed into a coping by conventional casting techniques, well known to those skilled in the dental arts. The invention may particularly be utilized with conventional PFM alloys, for example, having coefficients of thermal expansion (CTE) of about 14.0 µ/m/K at 500° C. As necessary, the components may be engineered by blending compositions and adjusting their expansion properties to meet the needs of a particular alloy. In general however, the invention may be utilized with current alloys without the need for a new and specialized alloy set.

The press to metal process for making PFM restorations is well known in the art. The invention and its components are readily adapted to the pressing process, providing a significantly improved efficiency to the medium pressure injection molding process.

In the press to metal process, a metal coping is placed in a mold. The coping is then coated with an opaquing porcelain which may be in powder or paste form, applied by spraying, a slurry dip, electrodeposit or in other forms or methods known to those skilled in the art. The opaquing is followed by wax-up and spruing to form a desired finished prosthesis form. The form is then invested, preferably in an all ceramic investment material, and the wax burned out, forming the prosthesis mold. An appropriate amount of integrated translucency porcelain component of the invention is then pressed into the mold, typically under the conditions shown in Table 1 below. The prosthesis is then divested of the molding material for finishing.

The compositions for utilization in the press to metal process are designed such that the prosthesis produced is directly a desired shade match. Of course, the aesthetics may be modified or improved by the use of small amounts of "enamel effect powders". These are typically applied in small sections at desired areas such as incisal edges, cusps, etc., followed by application of an overglaze or stains, as is well known in the art.

TABLE 1

PRESSING CONDITIONS

| Low temp. | High temp. | Heat rate | High temp. | Pressing | Pressure* |
|---|---|---|---|---|---|
| 700° C./ 1292° | 890° C./ 1634 | 60° C./ 108° F. | 20 min | 10 min | 4.25 bars |

*for Multimat Touch and Press System, use 2.5 bars

The integrated translucency composition of the invention is preferably utilized in the form of an ingot, preferably composed of a mixture of a dentin frit and a more transparent enamel frit. An example of a preferred frit formula for the ingot, as well as preferred ranges of compositions are listed in Table 2. To make the ingot material into a desired white porcelain, it is preferable to add 0.05% of antimony oxide ($Sb_2O_3$) and a fluorescing agent. The ingots are formed of the desired frits, typically in an amount of 2-5 grams, typically by pressing into a desired ingot form, pre-sintering at an initial temperature and further sintering at a higher temperature. The chemical compositions of the ingot white porcelain material together with the two raw frits are listed in Table 3.

TABLE 2

FRIT FORMULATION OF PORCELAIN INGOT MATERIAL

| Frit | Dentin Frit (Range) | Enamel Frit (Range) |
|---|---|---|
| Weight % | 78 (85-70) | 22 (15-30) |

TABLE 3

CHEMICAL COMPOSITION OF INGOT WHITE PORCELAIN (WT %)

| Oxide | Dentin Frit | Enamel Frit | Ingot white (Range) |
|---|---|---|---|
| $SiO_2$ | 64.5 | 64.7 | 64.5 (63-66) |
| $Al_2O_3$ | 10.8 | 17.2 | 12.2 (10-14) |
| $Na_2O$ | 8.1 | 2.5 | 6.9 (5-8) |
| $K_2O$ | 9.6 | 13.2 | 10.4 (9-12) |
| $Li_2O$ | — | 2.4 | 0.5 (0-2) |
| CaO | 3.4 | — | 2.6 (1-4 |
| BaO | 1.8 | — | 1.4 (0-3) |
| $Tb_4O_7$ | 1.8 | — | 1.4 (0-3) |
| $Sb_2O_3$ | | | 0.05 (0-1) |
| fluorescing agent | | | 0.05 (0-1) |
| Total | 100 | 100 | 100 |

The coping opaquer, in powder form, comprises mixing two frits with zirconia ($ZrO_2$). Preferred compositions and ranges are shown in Table 4 and the chemical compositions of powder opaques are listed in Table 5.

TABLE 4

FRIT FORMULATION OF POWDER OPAQUE

| Frit | Frit 1 | Frit 2 | Zirconia |
|---|---|---|---|
| Weight % | 50 (40-60) | 35 (30-45) | 15 (12-17) |

TABLE 5

CHEMICAL COMPOSITION OF POWDER OPAQUE (wt %)

| Oxide | Frit 1 | Frit 2 | Powder Opaque White (Range) |
|---|---|---|---|
| $SiO_2$ | 64.7 | 64.5 | 54.9 (53-56) |
| $Al_2O_3$ | 17.2 | 10.8 | 12.4 (10-14) |
| $Na_2O$ | 2.5 | 7.1 | 3.7 (3-5) |
| $K_2O$ | 13.2 | 8.7 | 9.6 (8-11) |
| $Li_2O$ | 2.4 | — | 1.2 (0-2) |
| CaO | — | 3.4 | 1.2 (0-2) |
| BaO | — | 1.8 | 0.6 (0-1) |
| $CeO_2$ | — | 1.9 | 0.7 (0-1.5) |
| $Tb_4O_7$ | — | 1.8 | 0.7 (0-1.5) |
| $ZrO_2$ | — | — | 15.0 (12-17) |
| Total | 100 | 100 | 100 |

An alternative coping opaquer, in paste form, also comprises two frits: Frit 1 and Frit 3, mixed with zirconia ($ZrO_2$), tin oxide ($SnO_2$), cerium oxide ($CeO_2$), titanium oxide ($TiO_2$), and antimony oxide ($Sb_2O_3$). The frit mixing formula is listed in Table 6 and the chemical composition of paste opaque is listed in Table 7.

TABLE 6

FRIT FORMULATION OF PASTE OPAQUE

| Frit | Frit 1 | Frit 3 | Zirconia | Tin | Cerium | Titanium | Antimony |
|---|---|---|---|---|---|---|---|
| Weight % | 47 (40- | 21 (20- | 27 (25- | 3 (0- | 1.5 (1- | 0.5 (0-1) | 0.05 (0-1) |

TABLE 7

CHEMICAL COMPOSITION OF PASTE OPAQUE (wt %)

| Oxide | Frit 1 | Frit 3 | Paste Opaque White |
|---|---|---|---|
| $SiO_2$ | 64.7 | 64.5 | 43.28 (42-45) |
| $Al_2O_3$ | 17.2 | 10.8 | 10.19 (8.5-11.5) |
| $Na_2O$ | 2.5 | 8.1 | 2.84 (2-4) |
| $K_2O$ | 13.2 | 9.6 | 8.10 (6-9) |
| $Li_2O$ | 2.4 | — | 1.11 (0.5-2) |
| CaO | — | 3.4 | 0.70 (0.5-2) |
| BaO | — | 1.8 | 0.37 (0-1) |
| $CeO_2$ | — | 1.3 | 1.75 (1-2) |
| $SnO_2$ | — | — | 2.95 (0-4) |
| $TiO_2$ | — | — | 0.49 (0-1) |
| $Sb_2O_3$ | — | 0.5 | 0.15 (0-1) |
| $ZrO_2$ | — | — | 26.59 (25-35) |
| Total | 100 | 100 | 100 |

FIG. 1 illustrates a dental prosthesis employing concepts of the present invention, which include a restoration 10 shown to be mounted in place on a prepared tooth 12. The prosthesis 10 includes a coping 14, which is covered by an opaque layer 16, which in turn is covered by a single porcelain layer 18.

What is claimed is:

1. Method of making a porcelain veneered dental prosthesis comprising the steps of:
   providing a substructure for supporting and fitting a dental prosthesis onto tooth surfaces;
   forming an opaquing ceramic mixture, wherein the opaquing ceramic mixture in powder form has the following total composition of 100 wt. %:
   53-56 wt % of $SiO_2$,
   10-14 wt % of $Al_2O_3$,
   3-5 wt % of $Na_2O$,
   8-11 wt % of $K_2O$,
   0-2 wt % of $Li_2O$,
   0-2 wt % of $CaO$,
   0-1 wt % of $BaO$,
   0-1.5 wt % of $CeO_2$, and
   0-3 wt % of $Tb_4O_7$,
   which is obtainable by mixing:
   (i) 40 to 60% by weight a first frit material, the first frit material being formed from a composition that includes a plurality of oxides;
   (ii) 20 to 45% by weight a second frit material, the second frit material being formed from a composition that includes a plurality of oxides, and
   (iii) 12-17 wt % $ZrO_2$;
   wherein the composition that forms the second frit material is different from the composition that forms the first frit material;
   coating the substructure with the opaquing ceramic mixture; and
   firing the substructure with the opaquing ceramic mixture to form an opaque layer fused to the substructure.

2. The method of claim 1, further comprising the step of providing in a hot press furnace for injecting a ceramic porcelain material into an investment mold.

3. The method of claim 1, further comprising the step of investing the dental substructure in a mold forming an adjacent cavity for receiving a veneer to be fused to the opaque layer of the substructure.

4. The method of claim 3, further comprising the step of injecting, under heat and pressure, into the veneer cavity a porcelain ceramic having an integrated tooth-like translucency wherein the porcelain ceramic forms a translucent layer that is fused to the opaque layer of the supporting structure or coping, thereby forming a finished prosthesis having a tooth-like appearance.

5. The method of claim 1, wherein the substructure is a metal supporting structure or coping.

6. The method of claim 1, wherein at least one of the composition of the first frit material and the second frit material further includes $ZrO_2$.

7. The method of claim 4, further comprising the step of forming the porcelain ceramic by blending dentin and enamel frit materials, in ratios of 70:30 to 85:15 percent by weight, respectively.

8. The method of claim 1, wherein the opaque layer is in powder form or in paste form.

9. The method of claim 1, wherein composition of the second frit material includes at least two of the following components:
   $CaO$,
   $BaO$,
   $CeO_2$, and
   $Tb_4O_7$.

10. The method of claim 1, wherein the composition of the second frit material includes at least two of the following components:
    $CaO$,
    $BaO$,
    $CeO_2$, and
    $Sb_2O_3$.

11. The method of claim 4, wherein the porcelain ceramic includes $Sb_2O_3$.

12. The method of claim 1, wherein the opaquing ceramic is applied by hand application using a spatula and/or a brush, spraying, a slurry dip or electrodeposit.

13. The method of claim 7, wherein the blend of the dentin frit material and the enamel frit material includes:
    70 to 85% by weight the dentin frit material; and
    15 to 30% by weight the enamel frit material, the enamel frit material being different than the dentin frit.

* * * * *